(12) United States Patent
Brann et al.

(10) Patent No.: US 9,702,864 B2
(45) Date of Patent: Jul. 11, 2017

(54) MEANS FOR GENERATING CELL-DISINTEGRATED BLOOD (71) Applicant: Thermo Finnigan LLC, San Jose, CA (US)

(72) Inventors: John E. Brann, Shrewsbury, MA (US); Joseph J. Takarewski, Jr., Brookline, MA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 14/578,136

(22) Filed: Dec. 19, 2014

(65) Prior Publication Data
US 2016/0178608 A1 Jun. 23, 2016

(51) Int. Cl.
G01N 33/49 (2006.01)
G01N 33/10 (2006.01)
(Continued)

(52) U.S. Cl.
CPC .......... G01N 33/492 (2013.01); G01N 30/88 (2013.01); G01N 33/491 (2013.01); G01N 33/80 (2013.01);
(Continued)

(58) Field of Classification Search
CPC .... G01N 33/492; G01N 33/491; G01N 33/49; G01N 33/487; G01N 33/48; G01N 33/1097; G01N 33/1095; G01N 33/10; G01N 33/00; G01N 2035/00475; G01N 2035/00465; Y10T 436/115831; Y10T 436/11; Y10T 436/00
USPC ...... 436/50, 43; 422/44, 50, 63, 59
See application file for complete search history.

(56) References Cited

U.S. PATENT DOCUMENTS 4,577,492 A * 3/1986 Holba ............... G01N 30/40 210/198.2
7,799,579 B2 9/2010 Seidel
(Continued)

FOREIGN PATENT DOCUMENTS

EP 1876450 A1 1/2008

OTHER PUBLICATIONS

Yu, Qianqian. "Configuration, optimization and evaluation of a novel instrumental platform for automated SPE-LC-MS/MS analysis of drugs in whole blood." Diss. Ludwig-Maximilians-Universität München, 2013, 143 pages.
(Continued)

Primary Examiner — Christine T Mui
(74) Attorney, Agent, or Firm — David A. Schell (57) ABSTRACT A method for analyzing a whole blood sample can include injecting whole blood into a first zone of a dual zone sample loop, applying sufficient heat or energy to the whole blood to disintegrate the cellular components of the whole blood sample to produce cell disintegrated blood, and injecting a sufficient volume of the buffer into the dual zone sample loop to move the cell disintegrated blood into a second zone of the dual zone sample loop. The method can further include switching a multiport value to an inject position, flowing the cell disintegrated blood from the dual zone sample loop into a solid phase extraction column, and eluting components of the cell disintegrated blood from the solid phase extraction column into a liquid chromatography column.

15 Claims, 5 Drawing Sheets (51) Int. Cl.
*G01N 35/10* (2006.01)
*G01N 33/80* (2006.01)
*G01N 30/88* (2006.01)
G01N 35/00 (2006.01)
G01N 1/44 (2006.01)
G01N 30/72 (2006.01)

(52) U.S. Cl.
CPC ..... *G01N 35/1016* (2013.01); *G01N 35/1097* (2013.01); *G01N 1/44* (2013.01); *G01N 30/7233* (2013.01); *G01N 2030/8822* (2013.01); *G01N 2035/00475* (2013.01)

(56) References Cited

U.S. PATENT DOCUMENTS

| | | |
|---|---|---|
| 8,231,838 B2 | 7/2012 | Seidel |
| 8,759,753 B1* | 6/2014 | Di Bussolo .......... B01D 15/325 210/198.2 |
| 2010/0311153 A1 | 12/2010 | Seidel |
| 2011/0229870 A1 | 9/2011 | Seidel |
| 2014/0299542 A1* | 10/2014 | Song ..................... G01N 30/00 210/635 |

OTHER PUBLICATIONS

Schebb et al.: "Development of an ultra fast online-solid phase extraction (SPE) liquid chromatography electrospray tandem mass spectrometry ( LC-ESI-MS/MS) based approach for the determination of drugs in pharmacokinetic studies", Analytical Methods, vol. 3, No. 2, 2011, pp. 420-428.

\* cited by examiner

MEANS FOR GENERATING CELL-DISINTEGRATED BLOOD

FIELD

The present disclosure generally relates to the field of mass spectrometry including systems and methods for generating cell-disintegrated blood.

INTRODUCTION

Identifying and quantifying analytes in samples from biological fluids can require complicated and tedious pretreatment procedures in order to remove cellular components from the fluid sample, such as erythrocytes, leukocytes and thrombocytes in whole blood. In order to analyze a blood sample, these cellular components may have to be removed by pre-treatment procedures such as centrifugation, filtration, sedimentation and/or homogenized by lysis using chemical reagents or mechanical treatment. These procedures, however, can be difficult to integrate into an automated test format. This holds also for a situation in which the target analytes are present in the cellular components, such as immuno-suppressive drugs in erythrocytes. In this case, the cellular components can be isolated or enriched by centrifugation and/or filtration prior to the addition of a lysis reagent or they can be denatured by addition of a denaturing agent to the original sample, for example a mixture of $ZnSO_4$ and acetonitrile, or the original sample is treated with temperatures of −20 to −170° C.

Liquid Chromatography (LC) can be used to separate the components in a mixture, to identify each component, and to quantify each component. It relies on pumps to pass a pressurized liquid solvent containing the sample mixture through a column filled with a solid adsorbent material. Each component in the sample can interact slightly differently with the adsorbent material, causing different migration rates for the different components and leading to the separation of the components as they flow out the column.

Mass spectrometry (MS) is widely used for identifying and quantifying compounds in a sample. In mass spectrometry, ions are separated according to their mass/charge (m/z) ratios, and ion abundances are measured as a function of m/z. Generally, a mass spectrometer has three major components: an ion source for producing ions, a mass analyzer for separating ions by m/z, and a detector for detecting the m/z-separated ions.

Liquid Chromatography combined with Mass Spectrometry (LC-MS) can provide for automated analysis of complex samples, first separating components based on the different migration rates through the chromatography column, and then identifying and quantifying the components of the sample with the mass spectrometer. However, biological samples with cellular components can be disruptive to fully automated analysis of the components in the sample, such as by requiring preprocessing to remove cellular components or fragments. An in-line system for processing whole blood to break down and remove residual cellular fragments would be desirable.

U.S. Pat. No. 7,799,579, hereby incorporated herein in its entirety by reference, discloses a process of heat treating biological samples under conditions that disintegrate the cellular components but avoid significant increases in the viscosity of sample. By maintaining the sample at a temperature between 60° C. and 90° C. for a period of time between 10 and 40 seconds, the cellular components of biological sample are substantially qualitatively disintegrated without causing substantial sedimentation, precipitation, denaturation, agglutination, or gelation of fluid components.

From the foregoing it will be appreciated that a need exists for improved systems and methods to can generate cell-disintegrated blood and provide fully automated analysis of whole blood.

SUMMARY

In a first aspect, a method of analyzing a whole blood sample can include loading a buffer, the whole blood sample, and an internal standard into a syringe or syringe loop, switching a multiport valve to a load position, injecting the internal standard and the whole blood into a first zone of a dual zone sample loop, apply sufficient heat or energy to the whole blood to disintegrate the cellular components of the whole blood sample to produce cell disintegrated blood, and injecting a sufficient volume of the buffer into the dual zone sample loop to move the cell disintegrated blood into a second zone of the dual zone sample loop. The method can further include switching the multiport value to an inject position, flowing the cell disintegrated blood from the dual zone sample loop into a solid phase extraction column, and eluting components of the cell disintegrated blood from the solid phase extraction column into a liquid chromatography column.

In various embodiments of the first aspect, the method can further include eluting components of the cell disintegrated blood from the liquid chromatography column to a mass analyzer.

In various embodiments of the first aspect, the method can further include identifying components of the cell disintegrated blood based on a retention time, a mass, a fragmentation mass, or any combination thereof.

In various embodiments of the first aspect, the whole blood sample can reside in the first zone for a time sufficient to disintegrate the cellular components of the whole blood sample.

In various embodiments of the first aspect, the whole blood sample can move through the first zone continuously. The flow rate and volume of the first zone can result in a dwell time of the whole blood sample within the first zone sufficient to disintegrate the cellular components of the whole blood sample.

In various embodiments of the first aspect, the whole blood sample can stop within the first zone for a time sufficient to disintegrate the cellular components of the whole blood sample prior to injecting the buffer to move the cell disintegrated blood to the second zone.

In a second aspect, a whole blood analysis system can include an injection syringe, a multiport valve, a loading pump, a dual zone sample loop comprising a first zone and a second zone, and a solid phase extraction column.

In various embodiments of the second aspect, the system can further include a liquid chromatography column.

In various embodiments of the second aspect, the system can further include a mass analyzer.

In various embodiments of the second aspect, the system can further include a controller configured to load a buffer and a whole blood sample into the syringe, switch the multiport valve to a load position, flow the whole blood sample from the syringe through the first zone of a dual zone sample loop into the second zone of the dual zone sample loop. Within the first zone, the whole blood sample can be exposed to a sufficient heat or energy for a sufficient time to disintegrate the cellular components of the whole blood sample to produce cell disintegrated blood. The controller can be further configured to switch the multiport value to an inject position, and activate the loading pump to flow the cell disintegrated blood from the dual zone sample loop through a solid phase extraction column to separate a subset of components from the cell disintegrated blood.

In various embodiments of the second aspect, the multiport valve can be configured to direct a fluid flow from the syringe into a first end of the dual zone sample loop adjacent to the first zone and out to waste from a second end of the dual zone sample loop adjacent to the second zone when in a load position, and to direct a fluid flow from the loading pump into the first end and out to the solid phase extraction column from the second end when in an inject position.

In a third aspect, a whole blood analysis system can include an injection syringe, a multiport valve, a dual zone sample loop comprising a first zone and a second zone, a solid phase extraction column, and a controller. The controller can be configured to load a buffer, the whole blood sample, and an internal standard into the syringe, switch the multiport valve to a load position, inject the internal standard and the whole blood into a first zone of a dual zone sample loop, applying sufficient heat or energy to the whole blood within the first zone to disintegrate the cellular components of the whole blood sample to produce cell disintegrated blood, and inject a sufficient volume of the buffer into the dual zone sample loop to move the cell disintegrated blood into a second zone of the dual zone sample loop. The controller can be further configured to switch the multiport value to an inject position, and flow the cell disintegrated blood from the dual zone sample loop into a solid phase extraction column to separate a liquid portion of the cell disintegrated blood from a solid portion of the cell disintegrated blood.

In various embodiments of the third aspect, the system can further include a liquid chromatography column. In particular embodiments, the controller can be further configured to flow the subset of components from the solid phase extraction column onto the liquid chromatography column.

In various embodiments of the third aspect, the system can further include a mass analyzer. In particular embodiments, the controller can be further configured to elute components of the cell disintegrated blood from the liquid chromatography column to the mass analyzer. Further, the controller can be further configured to identify components of the cell disintegrated blood based on a retention time, a mass, a fragmentation mass, or any combination thereof.

In various embodiments of the third aspect, the controller can be further configured to move the whole blood sample through the first zone in a continuous flow. The flow rate and volume of the first zone can result in a dwell time of the whole blood sample within the first zone sufficient to disintegrate the cellular components of the whole blood sample.

In various embodiments of the third aspect, the controller can be configured to stop the flow after injecting the whole blood sample into the first zone and prior to injecting the buffer. The flow can be stopped while the whole blood sample is within the first zone and for a time sufficient to disintegrate the cellular components of the whole blood sample.

In various embodiments of the third aspect, when the multiport valve is in the load position, fluid flows from the syringe into a first end of the dual zone sample loop adjacent to the first zone and out to waste from a second end of the dual zone sample loop adjacent to the second zone, and, when the multiport valve is in the inject position fluid, flows from a pump into the first end and out to the solid phase extraction column from the second end.

DRAWINGS

For a more complete understanding of the principles disclosed herein, and the advantages thereof, reference is now made to the following descriptions taken in conjunction with the accompanying drawings, in which.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for generating cell-disintegrated blood are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Whole Blood Analysis System

Figure 1:
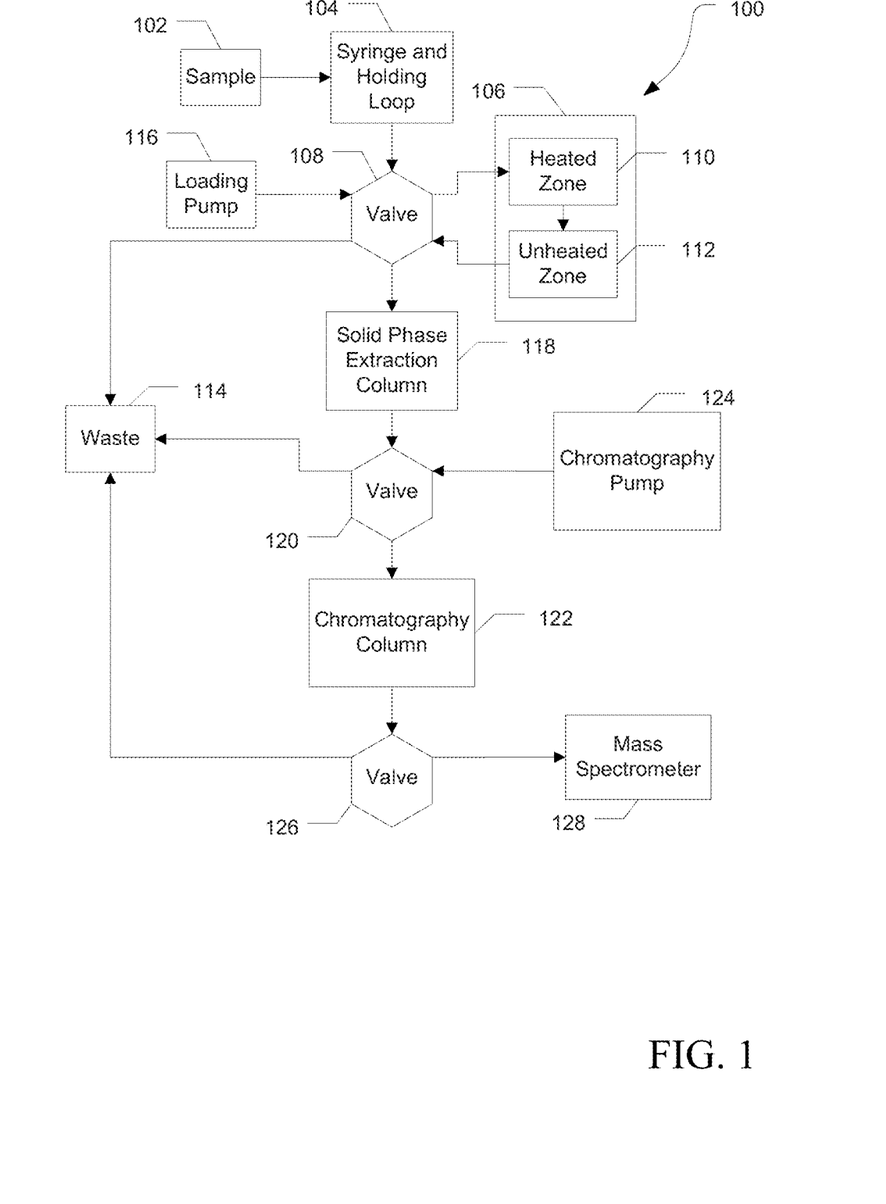
FIG. 1 is a block diagram illustrating an exemplary system for analyzing whole blood, in accordance with various embodiments.

FIG. 1 is a block diagram illustrating a system 100 for analyzing a whole blood sample 102. The system 100 can include a syringe and holding loop 104. The syringe and holding loop 104 can draw up at least a portion of the sample 102. In various embodiments, the syringe and holding loop 104 can be part of an auto-sampler configured to sequentially process multiple samples for analysis without the need for manual intervention. The syringe and holding loop 104 can supply the whole blood sample to a dual zone sample loop 106, by way of a multiport valve 108. The dual zone sample loop 106 can include a first zone 110 and a second zone 112. Heat or energy can be supplied to the whole blood sample within the first zone. In various embodiments, heat or energy can be supplied to the whole blood sample by using a heated water bath or a heated dry bath surrounding the first zone. Alternatively, inductive or resistive heating of the first zone can be used. In yet further embodiments, microwaves or infrared energy sources can be used. In various embodiments, even heating of the sample can be important to achieve disintegration of the cellular components without coagulation of the sample or portions thereof. The multiport valve 108 can direct liquid displaced from the dual zone sample loop to a waste 114.

With the portion of the sample 102 in the sample loop 106, the valve 108 can change position and a loading pump 116 can push the sample into a solid phase extraction column 118. Components of interest from the sample 102 can be retained by the solid phase extraction column 118 with other material directed by valve 120 to waste 114. As the components of interest exit the solid phase extraction column 118, valve 120 can redirect the flow to chromatography column 122.

With the components of interest loaded into chromatography column 122, valve 120 can direct a flow from a chromatography pump 124 through chromatography column 122. Chromatography column 122 can separate the components of interest and valve 126 can direct the components of interest to mass spectrometer 128. Valve 126 may also direct portions of the flow from chromatography column 122 that do not contain the components of interest to waste 114. Mass spectrometer 128 can identify and quantitate the components of interest.

Figure 2:
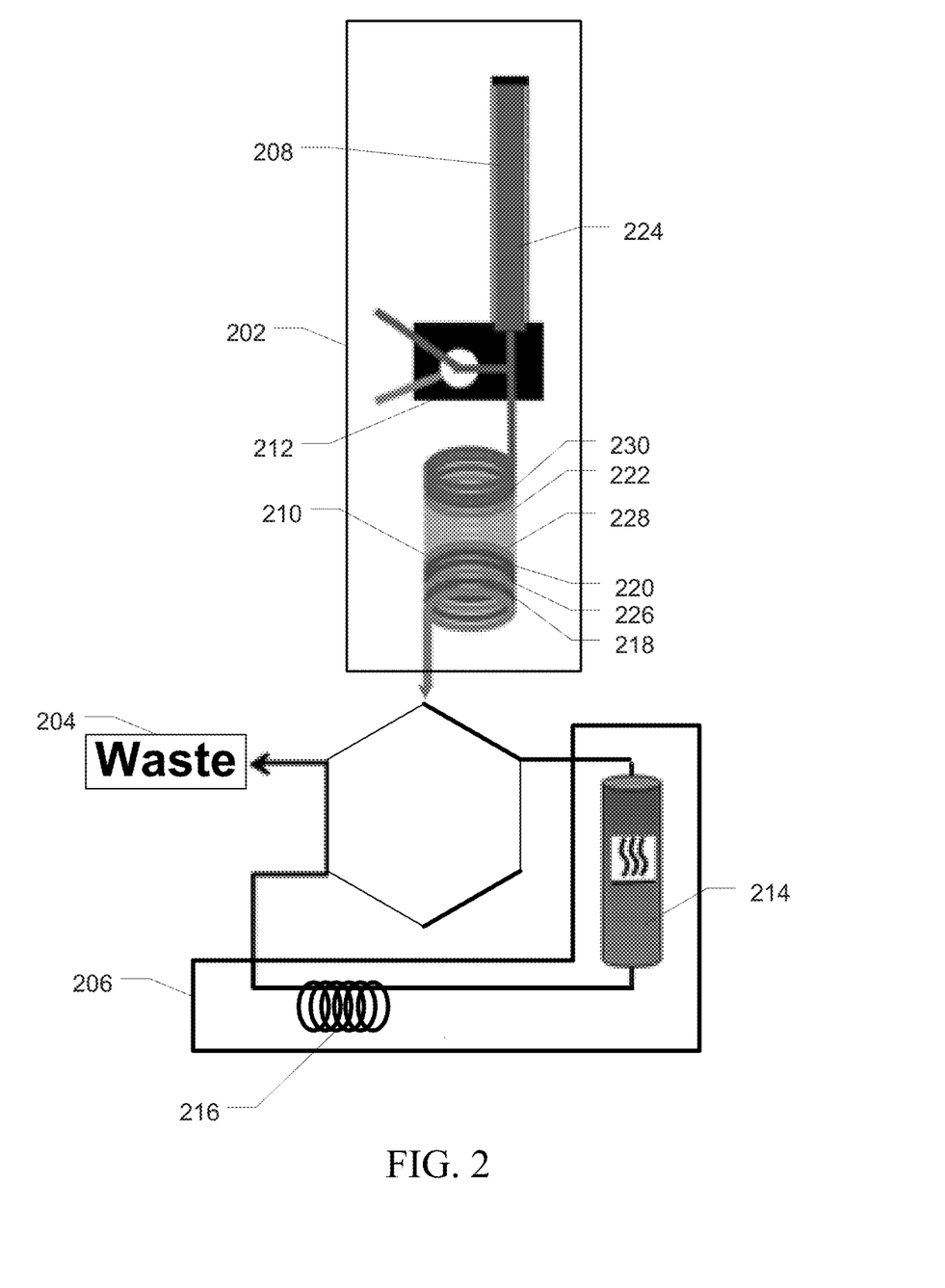
FIG. 2 is a diagram of an exemplary system for producing cell-disintegrated blood from a whole blood sample, in accordance with various embodiments.

FIG. 2 is a diagram illustrating a system 200 for heat treating whole blood to produce cell-disintegrated blood, which can be incorporated as part of system 100 depicted in FIG. 1. System 200 can include a syringe assembly 202, a multiport valve 204, and a dual zone injection loop 206. Syringe assembly 202 can include a barrel and plunger 208, a holding loop 210, and a solenoid 212. Dual zone injection loop 206 can include a first zone 214 and a second zone 216.

Syringe assembly 202 can load an internal standard 218, a whole blood sample 220, and loading buffer 222 into the holding loop 210. Additionally, the barrel and plunger 208 and part of the holding loop can be filled with a displacement fluid 224. Air volumes 226, 228, and 230 can be used to isolate the internal standard 218, whole blood sample 220, loading buffer 222, and displacement fluid 224 from each other. In various embodiments, isolating the whole blood sample 220 from the internal standard 218 and loading buffer 222 can prevent diffusion and can ensure the whole blood sample 220 is contained within a known volume. In various embodiments, solenoid 212 can be useful for adjusting the volume of the displacement fluid 224 within the syringe assembly 202 and for rinsing the inject value and loops.

Figure 3:
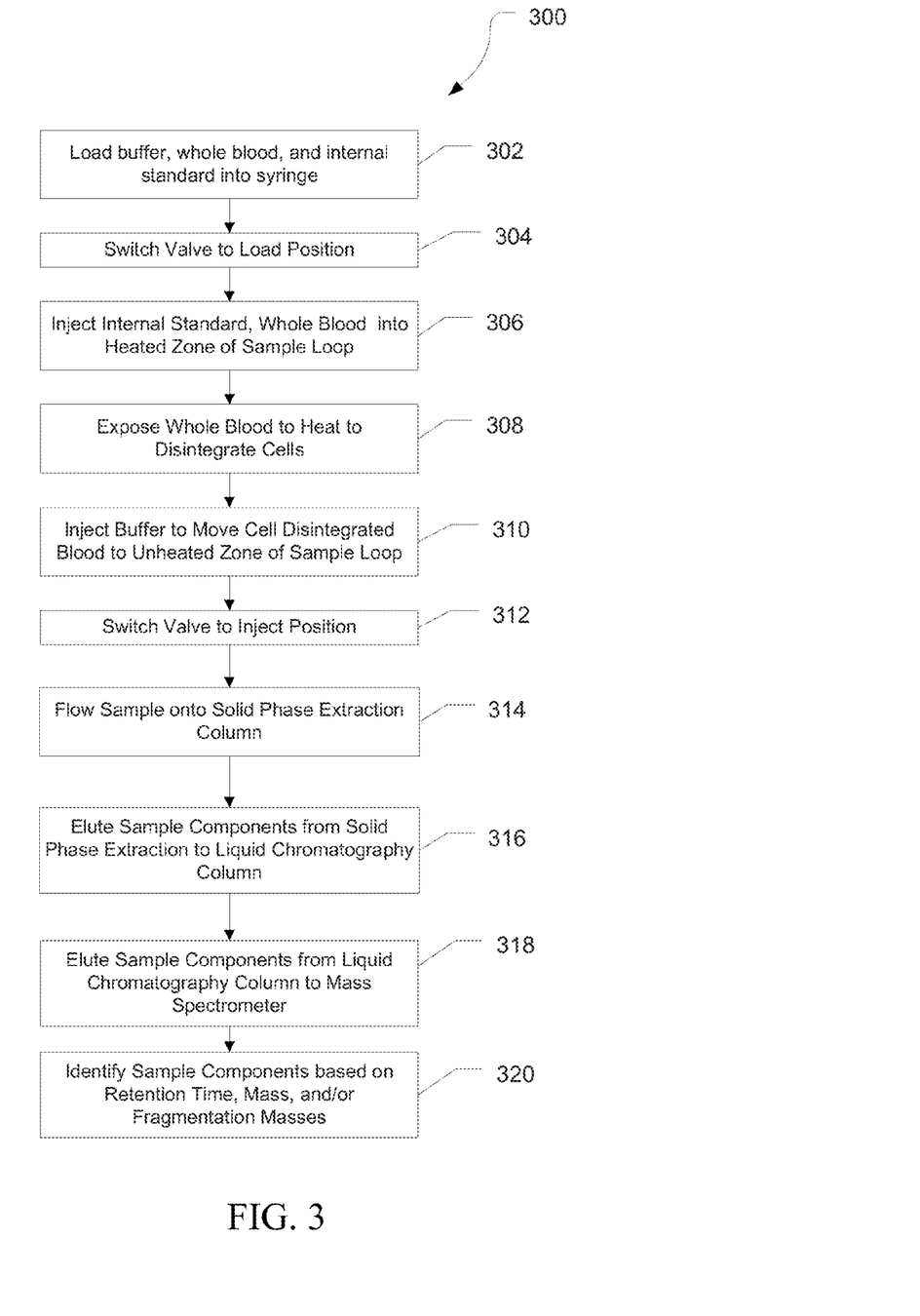
FIG. 3 is a flow diagram of an exemplary method for analyzing a whole blood sample, in accordance with various embodiments.

FIG. 3 is an exemplary flow diagram showing a method 300 for analyzing a whole blood sample. At 302, the whole blood sample can be loaded into a syringe, such as by an autosampler. In various embodiments, the syringe may include a sample loop, and the whole blood sample can be loaded into the sample loop portion of the syringe. The syringe may be further loaded with an internal standard which can be maintained separate from the whole blood sample with a volume of air. Additionally, the syringe can be further loaded with a volume of load buffer separated from the whole blood sample by a volume of air. In various embodiments, the syringe may be loaded in a last-in first-out (LIFO) order, such that the load buffer is drawn up first, followed by a volume of air, the whole blood sample, another volume of air, and the internal standard.

At 304, a multiport valve can be switched to a load position. The load position can allow fluid from the syringe to flow into the dual zone sample loop. Additionally, any liquid in the dual zone sample loop displaced by the fluid from the syringe can be directed to a waste port of the multiport valve. The load position can be configured to flow liquid into a first end of the dual zone sample loop nearest the first zone and for fluid to exit to waste from the other end closest to the second zone.

At 306, the whole blood sample can be injected into the first zone of the dual zone sample loop. In various embodiments, the internal standard can be injected first followed by the whole blood sample, maintaining the separation by virtue of the volume of air between them. While in the first zone of the dual zone sample loop, the whole blood can be exposed to heat or energy sufficient to disintegrate the cellular components of the whole blood without coagulating or causing the sample to gel to produce a cell-disintegrated blood sample, as shown at 308.

In various embodiments, heat or energy can be supplied from a heated water bath or a heated dry bath surrounding the first zone of the dual zone sample loop. Alternatively, energy can be supplied by inductive or resistive heating of the first zone. Care can be taken to avoid hot spots and to ensure even heating in order to achieve maximum disintegration of the cellular components without causing coagulation or gelling of the sample or portions thereof. In other embodiments, energy sources such as microwave sources or infrared sources can be used to supply energy to the whole blood sample within the first zone.

In various embodiments, the amount of energy supplied can be a function of both the energy input rate and the dwell time of the sample within the first zone. By way of example, at a temperature between about 64° C. and about 74° C., the dwell time could be between about 8 and about 51 seconds, such as 17 seconds at 70° C. However, various factors can influence the time and temperature needed to achieve the optimal heat transfer, such as the inner diameter, wall thickness, and material of the sample loop, type of energy source, and the like, and it may be necessary to empirically determine the time and temperature for optimal results. In various embodiments, the energy input rate can be a function of the temperature of a heated water bath or heated dry bath. In other embodiments, the energy input rate can be a function of the intensity of an energy source. The dwell time can be achieved during a continuous flow through the first zone by adjusting the volume of the first zone and the flow rate. Alternatively, the dwell time can be achieved, at least in part, by stopping the sample within the first zone.

At 310, the cell disintegrated blood sample can be moved from the first zone to the second zone of the dual zone sample loop by flowing load buffer into the dual zone sample loop. As previously mentioned, the movement of the cell disintegrated blood sample can occur continuously such that the dwell time of the sample is accomplished based on the volume of the first zone and the flow rate, or the movement can occur subsequent to application of energy by stopping the flow while the blood sample is in the first zone and restarting the flow after the blood sample has spent sufficient time in the first zone.

In various embodiments, the volume of load buffer injected into the sample loop can be sufficient to move the sample from the first zone to the second zone, but not so much as to move the sample or the internal standard out of the sample loop and to the waste. Additionally, the volume of the load buffer drawn up into the syringe can be sufficient to provide the volume to be injected into the sample loop.

At 312, the multiport valve can be switched to the inject position. In the inject position, liquid from a loading pump can flow through the dual zone sample loop to a solid phase extraction column. The inject position can be configured to flow liquid into a first end of the dual zone sample loop nearest the first zone and for fluid to exit to solid phase extraction column from the other end closest to the second zone. In this way, the dual zone sample loop can be configured in a first-in, first-out (FIFO) arrangement.

At 314, buffer from the loading pump can push the internal standard and cell disintegrated blood from the sample loop and into the solid phase extraction column. Components of interest from the cell disintegrated blood and the internal standard can adsorb onto the solid phase extraction column, while solid subcellular material can be filtered out and other components may be passed through the solid phase extraction column in an aqueous phase. In various embodiments, accumulated solid subcellular material can be removed from the filter and solid phase extraction column by reversing the fluid flow through the solid phase extraction column and directing the flow to waste.

At 316, the components of interest can be eluted from the solid phase extraction column and flow into the liquid chromatography column. In various embodiments, the elution can be achieved by altering the solvent being applied to the solid phase extraction column, such as by altering the pH, the salt concentration, or solvent polarity. Additionally, the components of interest can adsorb onto the column material of the chromatography column.

At 318, the components of interest can be eluted from the chromatography column. In various embodiments, the components of interest can be separated based on differences in the adsorption of the components to the column material. In various embodiments, the components can be eluted by varying the solvent conditions, either step-wise with a rapid change from one solvent condition to another or with a gradient where the relative concentrations of a first solution and a second solution are changed over time. In other embodiments, the solution conditions can remain the same. As the components of interest elute from the column, they can be directed to a mass spectrometer. The mass spectrometer can analyze the mass of ions generated from the components of interest, and can quantitate the amount of each component. At 320, the identity of each component of interest can be determined based on retention time in the liquid chromatography column, mass of the ions, mass of ions produced by fragmentation of the ions from the component of interest, or any combination thereof.

Mass Spectrometry Platforms

Figure 4:
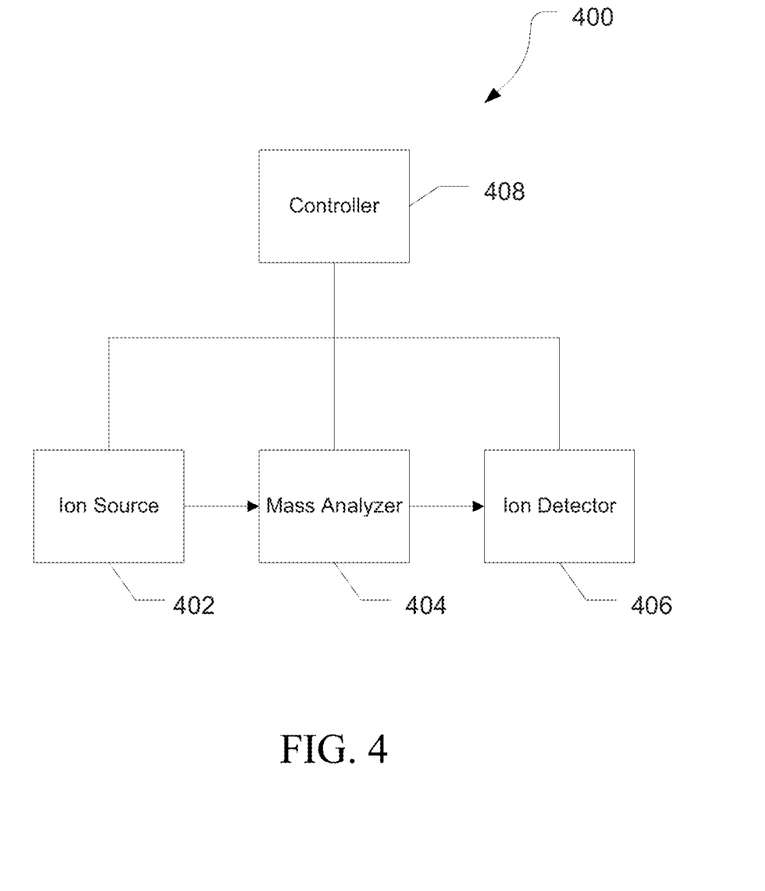
FIG. 4 is a block diagram illustrating an exemplary mass spectrometer, in accordance with various embodiments.

Various embodiments of mass spectrometry platforms 400 can include components as displayed in the block diagram of FIG. 4 as which may form all or part of mass spectrometer 128 depicted in FIG. 1. According to various embodiments, mass spectrometer 400 can include an ion source 402, a mass analyzer 404, an ion detector 406, and a controller 408.

In various embodiments, the ion source 402 generates a plurality of ions from a sample. The ion source can include, but is not limited to, a matrix assisted laser desorption/ionization (MALDI) source, electrospray ionization (ESI) source, inductively coupled plasma (ICP) source, electron ionization source, photoionization source, glow discharge ionization source, thermospray ionization source, and the like.

In various embodiments, the mass analyzer 404 can separate ions based on a mass to charge ratio of the ions. For example, the mass analyzer 404 can include a quadrupole mass filter analyzer, a time-of-flight (TOF) analyzer, a quadrupole ion trap analyzer, an electrostatic trap (e.g., Orbitrap) mass analyzer, and the like. In various embodiments, the mass analyzer 404 can also be configured to fragment the ions and further separate the fragmented ions based on the mass-to-charge ratio.

In various embodiments, the ion detector 406 can detect ions. For example, the ion detector 406 can include an electron multiplier, a Faraday cup, and the like. Ions leaving the mass analyzer can be detected by the ion detector. In various embodiments, the ion detector can be quantitative, such that an accurate count of the ions can be determined.

In various embodiments, the controller 408 can communicate with the ion source 402, the mass analyzer 404, and the ion detector 406. For example, the controller 408 can configure the ion source or enable/disable the ion source. Additionally, the controller 408 can configured the mass analyzer 404 to select a particular mass range to detect. Further, the controller 408 can adjust the sensitivity of the ion detector 406, such as by adjusting the gain. Additionally, the controller 408 can adjust the polarity of the ion detector 406 based on the polarity of the ions being detected. For example, the ion detector 406 can be configured to detect positive ions or be configured to detected negative ions.

Computer-Implemented System

Figure 5:
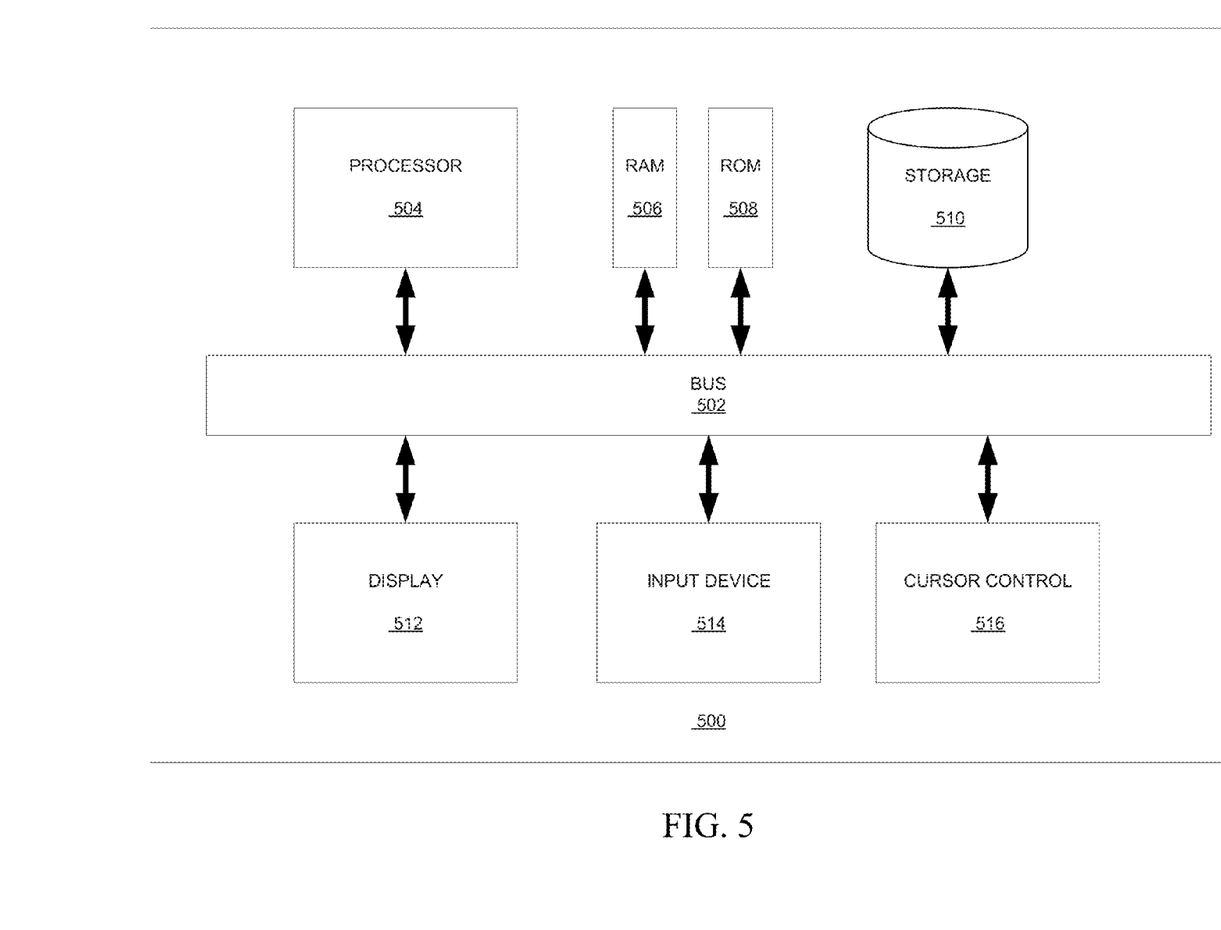
FIG. 5 is a block diagram illustrating an exemplary computer system, in accordance with various embodiments.

FIG. 5 is a block diagram that illustrates a computer system 500, upon which embodiments of the present teachings may be implemented as which may form all or part of controller 408 of mass spectrometry platform 400 depicted in FIG. 4. In various embodiments, computer system 500 can include a bus 502 or other communication mechanism for communicating information, and a processor 504 coupled with bus 502 for processing information. In various embodiments, computer system 500 can also include a memory 506, which can be a random access memory (RAM) or other dynamic storage device, coupled to bus 502 for determining base calls, and instructions to be executed by processor 504. Memory 506 also can be used for storing temporary variables or other intermediate information during execution of instructions to be executed by processor 504. In various embodiments, computer system 500 can further include a read only memory (ROM) 508 or other static storage device coupled to bus 502 for storing static information and instructions for processor 504. A storage device 510, such as a magnetic disk or optical disk, can be provided and coupled to bus 502 for storing information and instructions.

In various embodiments, processor 504 can include a plurality of logic gates. The logic gates can include AND gates, OR gates, NOT gates, NAND gates, NOR gates, EXOR gates, EXNOR gates, or any combination thereof. An AND gate can produce a high output only if all the inputs are high. An OR gate can produce a high output if one or more of the inputs are high. A NOT gate can produce an inverted version of the input as an output, such as outputting a high value when the input is low. A NAND (NOT-AND) gate can produce an inverted AND output, such that the output will be high if any of the inputs are low. A NOR (NOT-OR) gate can produce an inverted OR output, such that the NOR gate output is low if any of the inputs are high. An EXOR (Exclusive-OR) gate can produce a high output if either, but not both, inputs are high. An EXNOR (Exclusive-NOR) gate can produce an inverted EXOR output, such that the output is low if either, but not both, inputs are high.

TABLE 5

Logic Gates Truth Table

| INPUTS | | OUTPUTS | | | | | | |
|---|---|---|---|---|---|---|---|---|
| A | B | NOT A | AND | NAND | OR | NOR | EXOR | EXNOR |
| 0 | 0 | 1 | 0 | 1 | 0 | 1 | 0 | 1 |
| 0 | 1 | 1 | 0 | 1 | 1 | 0 | 1 | 0 |
| 1 | 0 | 0 | 0 | 1 | 1 | 0 | 1 | 0 |
| 1 | 1 | 0 | 1 | 0 | 1 | 0 | 0 | 1 |

One of skill in the art would appreciate that the logic gates can be used in various combinations to perform comparisons, arithmetic operations, and the like. Further, one of skill in the art would appreciate how to sequence the use of various combinations of logic gates to perform complex processes, such as the processes described herein.

In an example, a 5-bit binary comparison can be performed using a XNOR gate since the result is high only when the two inputs are the same. A comparison of two multi-bit values can be performed by using multiple XNOR gates to compare each pair of bits, and the combining the output of the XNOR gates using and AND gates, such that the result can be true only when each pair of bits have the same value. If any pair of bits does not have the same value, the result of the corresponding XNOR gate can be low, and the output of the AND gate receiving the low input can be low.

In another example, a 5-bit adder can be implemented using a combination of AND gates and XOR gates. Specifically, the 5-bit adder can receive three inputs, the two bits to be added (A and B) and a carry bit (Can), and two outputs, the sum (S) and a carry out bit (Cout). The Cin bit can be set to 0 for addition of two one bit values, or can be used to couple multiple 5-bit adders together to add two multi-bit values by receiving the Cout from a lower order adder. In an exemplary embodiment, S can be implemented by applying the A and B inputs to a XOR gate, and then applying the result and Cin to another XOR gate. Cout can be implemented by applying the A and B inputs to an AND gate, the result of the A-B XOR from the SUM and the Cin to another AND, and applying the input of the AND gates to a XOR gate.

TABLE 2

5-bit Adder Truth Table

| INPUTS | | | OUTPUTS | |
|---|---|---|---|---|
| A | B | Cin | S | Cout |
| 0 | 0 | 0 | 0 | 0 |
| 1 | 0 | 0 | 0 | 1 |
| 0 | 1 | 0 | 0 | 1 |
| 1 | 1 | 0 | 1 | 0 |
| 0 | 0 | 1 | 0 | 1 |
| 1 | 0 | 1 | 1 | 0 |
| 0 | 1 | 1 | 1 | 0 |
| 1 | 1 | 1 | 1 | 1 |

In various embodiments, computer system 500 can be coupled via bus 502 to a display 512, such as a cathode ray tube (CRT) or liquid crystal display (LCD), for displaying information to a computer user. An input device 514, including alphanumeric and other keys, can be coupled to bus 502 for communicating information and command selections to processor 504. Another type of user input device is a cursor control 516, such as a mouse, a trackball or cursor direction keys for communicating direction information and command selections to processor 504 and for controlling cursor movement on display 512. This input device typically has two degrees of freedom in two axes, a first axis (i.e., x) and a second axis (i.e., y), that allows the device to specify positions in a plane.

A computer system 500 can perform the present teachings. Consistent with certain implementations of the present teachings, results can be provided by computer system 500 in response to processor 504 executing one or more sequences of one or more instructions contained in memory 506. Such instructions can be read into memory 506 from another computer-readable medium, such as storage device 510. Execution of the sequences of instructions contained in memory 506 can cause processor 504 to perform the processes described herein. In various embodiments, instructions in the memory can sequence the use of various combinations of logic gates available within the processor to perform the processes describe herein. Alternatively hardwired circuitry can be used in place of or in combination with software instructions to implement the present teachings. In various embodiments, the hard-wired circuitry can include the necessary logic gates, operated in the necessary sequence to perform the processes described herein. Thus implementations of the present teachings are not limited to any specific combination of hardware circuitry and software.

The term "computer-readable medium" as used herein refers to any media that participates in providing instructions to processor 504 for execution. Such a medium can take many forms, including but not limited to, non-volatile media, volatile media, and transmission media. Examples of non-volatile media can include, but are not limited to, optical or magnetic disks, such as storage device 510. Examples of volatile media can include, but are not limited to, dynamic memory, such as memory 506. Examples of transmission media can include, but are not limited to, coaxial cables, copper wire, and fiber optics, including the wires that comprise bus 502.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, G, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

Results

A sample loop of stainless HPLC grade steel tubing having an outer diameter of 1/16 inch and an inner diameter of 0.020 inch is tested. 25 cm of the sample loop is submerged in a heated bath to form a heated zone, providing a calculate volume of 50.6 µL. The bath is a mechanically stirred temperature controlled bath that contains 300 mL of polyethylene glycol 400. The results are summarized in Table 1.

TABLE 1

| Temperature (° C.) | Flow Rate (µL/s) | Dwell Time (sec) | Result |
|---|---|---|---|
| 64 | 6.5 | 8 | Incomplete Disintegration |
| 64 | 3 | 17 | Disintegration |
| 64 | 1 | 51 | Disintegration |
| 70 | 6.5 | 8 | Disintegration |
| 70 | 3 | 17 | Disintegration |
| 70 | 1 | 51 | Disintegration |
| 74 | 6.5 | 8 | Disintegration |
| 74 | 3 | 17 | Disintegration |
| 74 | 1 | 51 | Partial Gelation |

What is claimed is:

1. A method of analyzing an intact whole blood sample, comprising:
sequentially loading a buffer, the intact whole blood sample, and an internal standard into a syringe assembly;
switching a multiport valve to a load position;
injecting the sequentially loaded internal standard and intact whole blood sample into a first zone of a dual zone sample loop;
applying sufficient energy to the intact whole blood sample within the first zone of the dual zone sample loop to disintegrate the cellular components of the intact whole blood sample to produce cell disintegrated blood;
injecting a sufficient volume of the buffer into the dual zone sample loop to move the cell disintegrated blood into a second zone of the dual zone sample loop;
switching the multiport value to an inject position;
flowing the cell disintegrated blood from the dual zone sample loop into a solid phase extraction column; and
eluting components of the cell disintegrated blood from the solid phase extraction column into a liquid chromatography column.

2. The method of claim 1, further comprising eluting components of the cell disintegrated blood from the liquid chromatography column to a mass analyzer.

3. The method of claim 1, further comprising identifying components of the cell disintegrated blood based on a retention time, a mass, a fragmentation mass, or any combination thereof.

4. The method of claim 1, wherein the whole blood sample is resident in the first zone for a time sufficient to disintegrate the cellular components of the whole blood sample.

5. The method of claim 1, wherein the whole blood sample moves through the first zone continuously, the flow rate and volume of the first zone resulting in a dwell time of the whole blood sample within the first zone sufficient to disintegrate the cellular components of the whole blood sample.

6. The method of claim 1, wherein the whole blood sample stops within the first zone for a time sufficient to disintegrate the cellular components of the whole blood sample prior to injecting the buffer to move the cell disintegrated blood to the second zone.

7. A whole blood analysis system comprising:
an injection syringe assembly;
a multiport valve;
a dual zone sample loop comprising a first zone and a second zone;
a solid phase extraction column; and
a controller configured to:
sequentially load a buffer, an intact whole blood sample, and an internal standard into the syringe assembly;
switch the multiport valve to a load position;
inject the sequentially loaded internal standard and whole blood into a first zone of a dual zone sample loop;
applying sufficient heat to the intact whole blood sample within the first zone of the dual zone sample loop to disintegrate the cellular components of the whole blood sample to produce cell disintegrated blood;
inject a sufficient volume of the buffer into the dual zone sample loop to move the cell disintegrated blood into a second zone of the dual zone sample loop;
switch the multiport value to an inject position; and
flow the cell disintegrated blood from the dual zone sample loop into a solid phase extraction column to isolate a subset of components from the cell disintegrated blood.

8. The system of claim 7, further comprising a liquid chromatography column.

9. The system of claim 8, wherein the controller is further configured to flow elute the subset of components onto the liquid chromatography column.

10. The system of claim 9, further comprising a mass analyzer.

11. The system of claim 10, wherein the controller is further configured to elute components of the cell disintegrated blood from the liquid chromatography column to the mass analyzer.

12. The system of claim 11, wherein the controller is further configured to identify components of the cell disintegrated blood based on a retention time, a mass, a fragmentation mass, or any combination thereof.

13. The system of claim 7, wherein the controller is configured to move the whole blood sample through the first zone in a continuous flow, the flow rate and volume of the first zone resulting in a dwell time of the whole blood sample within the first zone sufficient to disintegrate the cellular components of the whole blood sample.

14. The system of claim 7, wherein the controller is configured to stop the flow after injecting the whole blood sample into the first zone and prior to injecting the buffer, the flow being stopped while the whole blood sample is within the first zone and for a time sufficient to disintegrate the cellular components of the whole blood sample.

15. The system of claim 7, wherein when the multiport valve is in the load position a fluid flow is from the syringe assembly into a first end of the dual zone sample loop adjacent to the first zone and out to waste from a second end of the dual zone sample loop adjacent to the second zone, and when the multiport value is in the inject position the fluid flow is from a pump into the first end of the dual zone sample loop and out to the solid phase extraction column from the second end of the dual zone sample loop.

* * * * *

UNITED STATES PATENT AND TRADEMARK OFFICE
CERTIFICATE OF CORRECTION

PATENT NO. : 9,702,864 B2
APPLICATION NO. : 14/578136
DATED : July 11, 2017
INVENTOR(S) : John E. Brann et al.

Page 1 of 1

It is certified that error appears in the above-identified patent and that said Letters Patent is hereby corrected as shown below:

In the Claims

Claim 1, Column 12, Line 62:
Replace "switching the multiport value to an inject position"
With --switching the multiport valve to an inject position--

Claim 7, Column 14, Line 1:
Replace "switch the multiport value to an inject position"
With --switch the multiport valve to an inject position--

Claim 15, Column 14, Line 39:
Replace "and when the multiport value is in the inject position"
With --and when the multiport valve is in the inject position--

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*